US00PP35454P3

(12) United States Plant Patent
Janssen et al.

(10) Patent No.: US PP35,454 P3
(45) Date of Patent: Nov. 7, 2023

(54) APPLE TREE NAMED 'GALA MGCP'

(50) Latin Name: ***Malus domestica* Borkh.**
Varietal Denomination: GALA MGCP

(71) Applicants: BOOMKWEKERIJEN GEBR. JANSSEN B.V., Nederweert (NL); VISSERS ORCHARD & NURSERY INC., Grey Highlands (CA)

(72) Inventors: Paulus Paulus Mathieu Jacobus Hermanus Janssen, Nederweert (NL); Cornelis Aloysius Johannes Vissers, Grey Highlands (CA)

(73) Assignees: BOOMKWEKERIJN GEBR. JANSSEN B.V., Nederweert (NL); VISSERS ORCHARD & NURSERY INC., Grey Highlands (CA)

( * ) Notice: Subject to any disclaimer, the term of this patent is extended or adjusted under 35 U.S.C. 154(b) by 0 days.

(21) Appl. No.: 17/971,589

(22) Filed: Oct. 22, 2022

(65) Prior Publication Data

US 2023/0132406 P1 Apr. 27, 2023

Related U.S. Application Data

(60) Provisional application No. 63/271,145, filed on Oct. 23, 2021.

(51) Int. Cl.
*A01H 5/08* (2018.01)
*A01H 6/74* (2018.01)

(52) U.S. Cl.
USPC ..... Plt./162
CPC ..... *A01H 6/7418* (2018.05)

(58) Field of Classification Search
USPC ..... Plt./162
CPC ..... A01H 6/7418; A01H 5/08
See application file for complete search history.

*Primary Examiner* — Keith O. Robinson
(74) *Attorney, Agent, or Firm* — C. Anne Whealy

(57) ABSTRACT

A new and distinct cultivar of Apple tree named 'GALA MGCP', characterized by its upright to outwardly spreading plant habit; moderately vigorous growth habit; after flower senescence, receptacles are reddish pink in color; relatively early fruit-coloring; numerous fruit produced per plant; and high quality fruits that are yellow in color heavily blushed with red.

4 Drawing Sheets

Figure 1:
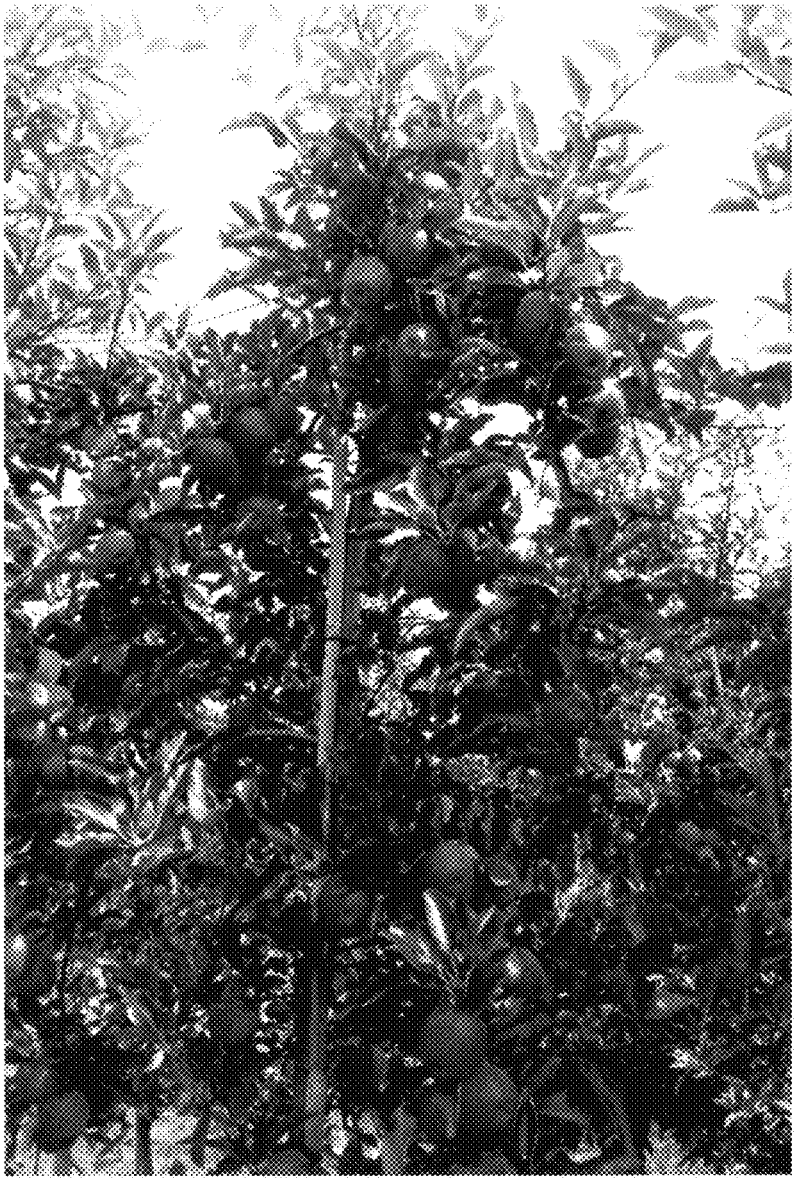

Botanical designation: *Malus domestica* Borkh.
Cultivar denomination: 'GALA MGCP'.

An European Community Plant Breeder's Rights application for the instant plant was filed by the Applicants/Assignees on Jul. 11, 2018, application number 2018/2943. Foreign priority is not claimed to this application.

BACKGROUND OF THE INVENTION

The present invention relates to a new and distinct cultivar of Apple tree, botanically known as *Malus domestica* Borkh. and hereinafter referred to by the name 'GALA MGCP'.

The new Apple tree is a whole plant mutation of *Malus domestica* Borkh. 'GALA MITCHGLA', not patented. The new Apple tree was discovered and selected by the Inventors as a single plant within a population of trees of 'GALA MITCHGLA' grown in a controlled environment in Grey Highlands, Ontario, Canada in 2013.

Asexual reproduction of the new Apple tree by grafting in a controlled environment in Nederweert, The Netherlands since the spring of 2016 has shown that the unique features of this new Apple tree are stable and reproduced true to type in successive generations.

SUMMARY OF THE INVENTION

The new Apple tree has not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'GALA MGCP'. These characteristics in combination distinguish 'GALA MGCP' as a new and distinct Apple tree:

1. Upright to outwardly spreading plant habit.
2. Moderately vigorous growth habit.
3. After flower senescence, receptacles are reddish pink in color.
4. Relatively early fruit-coloring.
5. Numerous fruit produced per plant.
6. High quality fruits that are yellow in color heavily blushed with red.

Trees of the new Apple differ primarily from trees of the mutation parent, 'GALA MITCHGLA', in the following characteristics:

1. Fruits of trees of the new Apple color about two to three weeks earlier than fruits of trees of 'GALA MITCHGLA'.
2. Fruits of trees of the new Apple are more red in color than fruits of trees of 'GALA MITCHGLA'.
3. Fruits of trees of the new Apple do not have stripes whereas fruits of trees of 'GALA MITCHGLA' have stripes.

Trees of the new Apple can be compared to trees of *Malus domestica* 'Gala', disclosed in U.S. Plant Pat. No. 3,637. In side-by-side comparisons, trees of the new Apple differ primarily from trees of 'Gala' in the following characteristics:

1. Fruits of trees of the new Apple color earlier than fruits of trees of 'Gala'.
2. Fruits of trees of the new Apple are more red in color than fruits of trees of 'Gala'.
3. After flower senescence, receptacles of trees of the new Apple are reddish pink in color whereas receptacles of trees of 'Gala' are yellowish green in color.

BRIEF DESCRIPTION OF THE PHOTOGRAPHS

The accompanying photographs illustrate the overall appearance of the new Apple tree showing the colors as true as it is reasonably possible to obtain in colored reproductions of this type. Colors in the photographs may differ slightly from the color values cited in the detailed botanical description which accurately describe the colors of the new Apple tree.

The photograph on the first sheet (FIG. 1) is a side perspective view of a typical tree of 'GALA MGCP' grown in an outdoor orchard.

Figure 2:
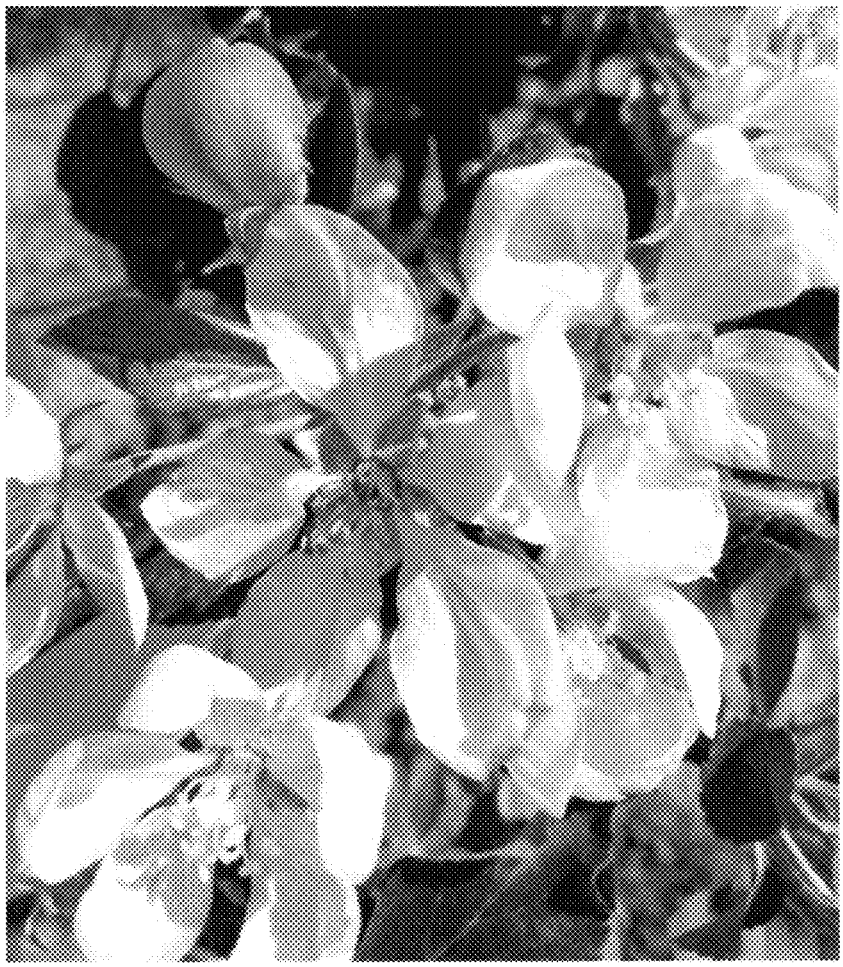

The photograph on the second sheet (FIG. 2) is a close-up view of a typical flowering branch of 'GALA MGCP'.

Figure 3:
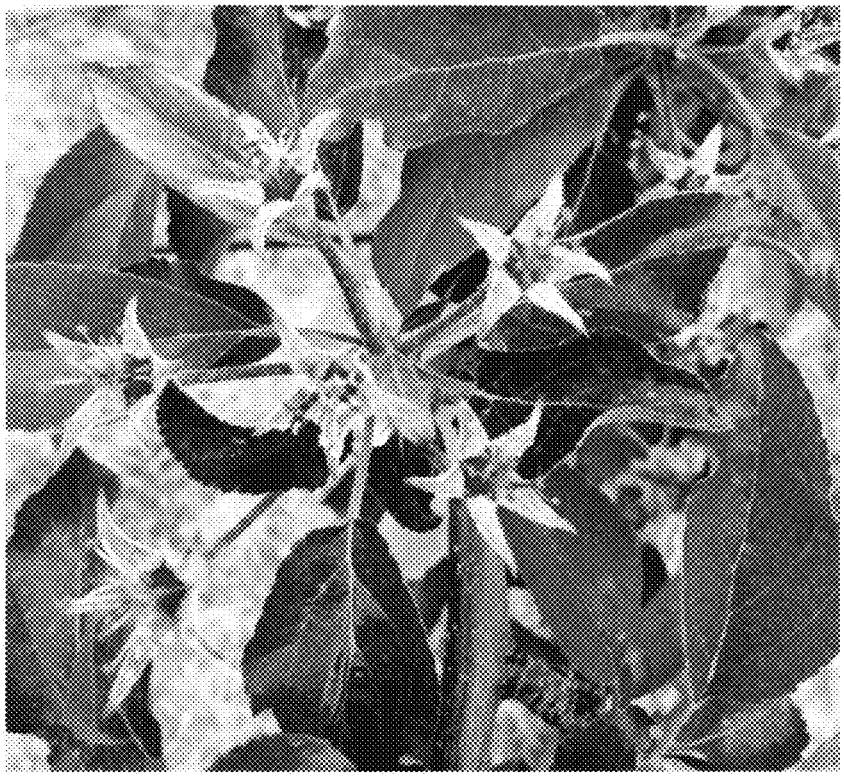

The photograph on the third sheet (FIG. 3) is a close-up view of typical receptacles of 'GALA MGCP' after the flowers have senesenced.

Figure 4:
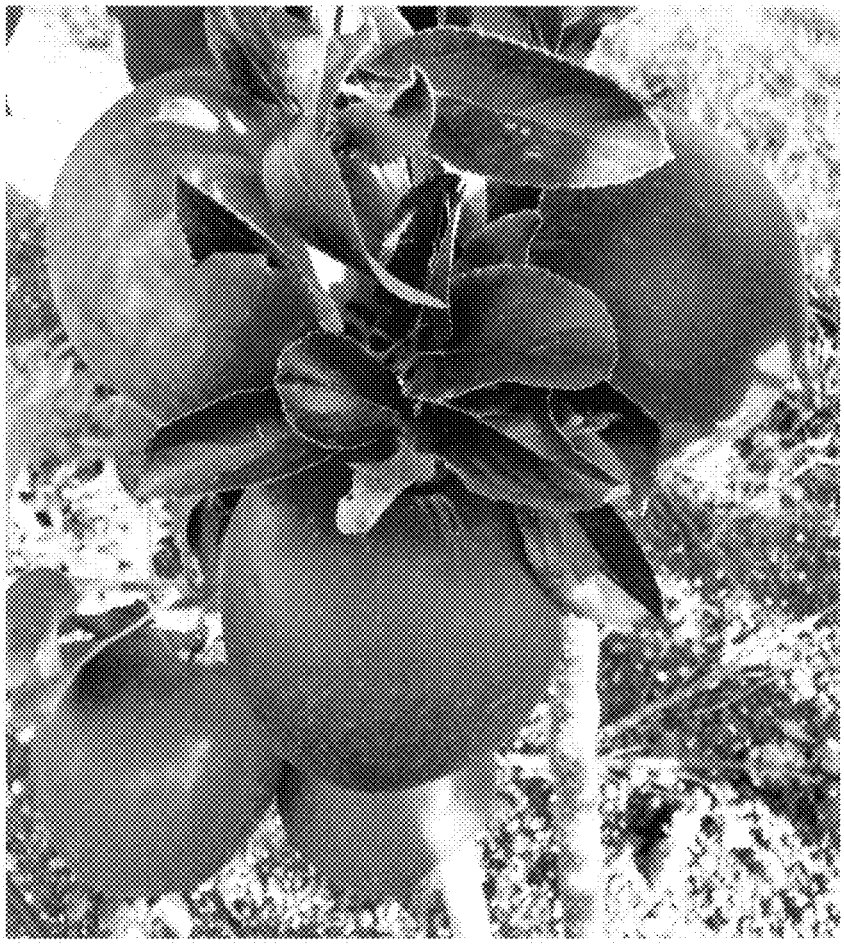

The photograph on the fourth sheet (FIG. 4) is a close-up view of typical fruits of 'GALA MGCP'.

DETAILED BOTANICAL DESCRIPTION

The aforementioned photographs, following observations and measurements describe trees grown during the late summer in Nederweert, The Netherlands in an outdoor orchard and under cultural practices typical of commercial Apple tree production. Trees were two or three years old when the photographs and description were taken. During the production of the trees, day temperatures ranged from 10 C to 30 C and night temperatures ranged from 8 C to 15 C. Measurements and numerical values represent averages for typical trees and tree parts. The actual measurements of any individual tree or tree parts, or any group of trees or tree parts, of the new Apple tree may vary from the stated average. In the following description, color references are made to The Royal Horticultural Society Colour Chart, 2001 Edition, except where general terms of ordinary dictionary significance are used.

Botanical classification: *Malus domestica* Borkh. 'GALA MGCP'.

Parentage: Whole plant mutation of *Malus domestica* Borkh. 'GALA MITCHGLA', not patented.

Propagation:

*Type*.—Typically by grafting onto a rootstock.

Plant description:

*Plant and growth habit*.—Upright to outwardly spreading plant habit; moderately vigorous growth habit and moderate growth rate.

*Tree height*.—About three meters.

*Tree diameter*.—About 1 meter to 1.5 meter.

*Growth rate*.—About 20 cm to 30 cm per year.

*Lateral branch description*.—Length: About 40 cm to 70 cm. Diameter: About 3 cm to 5 cm. Internode length: About 3 cm to 10 cm. Strength: Strong, firm. Angle of attachment: About 60 to 75 degrees from main trunk axis. Texture: Glabrous; woody and slightly rough. Color: Close to 166A variably flushed with close to 178B. Lenticels: Density: Moderate to dense. Color: Pale brown, close to 199D.

*Leaf description*.—Arrangement: Alternate; simple. Length: About 7 cm to 10 cm. Width: About 4 cm to 6 cm. Shape: Ovate to obovate. Apex: Acute. Base: Obtuse to slightly cordate. Margin: Crenate to serrate; undulate. Texture, upper surface: Smooth, glabrous. Texture, lower surface: Rough, pubescent. Venation pattern: Pinnate. Color: Developing leaves, upper surface: Close to 144B. Developing leaves, lower surface: Close to 144C. Fully developed leaves, upper surface: Close to 143A; venation, close to 145A. Fully developed leaves, lower surface: Close to 143C; venation, close to 147D. Petioles: Length: About 3 cm to 5 cm. Diameter: About 2 mm to 4 mm. Texture, upper and lower surfaces: Smooth, glabrous. Color, upper and lower surfaces: Close to between 141C and 143A variably flushed with greyed green, close to 194D.

Flower description:

*Flower type and flowering habit*.—Single rotate flowers arranged on panicles; freely flowering habit with about six to ten flowers per inflorescence; flowers face mostly outwardly.

*Fragrance*.—Faintly fragrant, pleasant.

*Natural flowering season*.—Continuously flowering in April and May in The Netherlands.

*Flower longevity*.—Flowers last about 1.5 to 2 weeks on the plant; flowers not persistent.

*Inflorescence height*.—About 4 cm to 6 cm.

*Inflorescence diameter*.—About 4 cm to 6 cm.

*Flower diameter*.—About 2 cm to 4 cm.

*Flower depth* (*height*).—About 5 mm to 10 mm.

*Flower buds*.—Length: About 1 cm to 2 cm. Diameter: About 1 cm to 2 cm. Shape: Round to oval. Texture: Smooth, glabrous. Color: Close to between 58C and 63C.

*Petals*.—Quantity and arrangement: Typically five in a single whorl; not imbricate. Length: About 1 cm to 2 cm. Width: About 1 cm to 2 cm. Shape: Obovate. Apex: Obtuse. Base: Cordate. Margin: Entire. Texture, upper and lower surfaces: Smooth, glabrous; satiny. Color: When opening, upper and lower surfaces: Close to 155C slightly tinged with close to 63C. Fully opened, upper surface: Close to 155C. Fully opened, lower surface: Close to 155C slightly tinged with close to 63C.

*Sepals*.—Quantity and arrangement: Typically five in a single whorl. Length: About 4 mm to 6 mm. Width: About 2 mm to 4 mm. Shape: Ovate. Apex: Acute to obtuse. Base: Cordate. Margin: Entire. Texture, upper and lower surfaces: Smooth, glabrous. Color, upper surface: Close to 144B. Color, lower surface: Close to 144B; towards the apex, slightly tinged with close to 187A.

*Pedicels*.—Length: About 2 cm to 4 cm. Diameter: About 1 mm to 2 mm. Strength: Moderately strong. Aspect: About 60 to 90 degrees from stem. Texture: Smooth, glabrous. Color: Close to 146D tinged with close to 187A.

*Reproductive organs*.—Stamens: Quantity: About 20 per flower. Filament length: About 2 cm to 3 cm. Filament color: Close to 155A. Anther length: About 5 mm to 10 mm. Anther shape: Bi-lobed. Anther color: Close to 15A. Pollen amount: Scarce. Pollen color: Close to 158A. Pistils: Quantity: About five per flower. Pistil length: About 1 cm. Stigma shape: Trumpet-shaped. Stigma color: Close to 144D. Style length: Less than 1 cm. Style color: Close to 144C to 144D. Ovary color: Close to 144D.

Fruit description:

*Ripening time*.—About 160 to 170 days.

*Postproduction longevity*.—About one year in cold storage.

*Yield*.—Higher than average, about 20 to 25 kilos per tree.

*Use*.—Fresh market.

*Length*.—About 7 cm to 8 cm.

*Diameter*.—About 7 cm to 8 cm.

*Fruit weight*.—Typically individual fruits will weigh between 160 to 190 gr depending on environmental conditions.

*General shape in profile*.—Conic.

*Depth of cavity*.—Flat to medium, about 1 cm.

*Width of cavity*.—About 2.5 cm.

*Basin*.—Medium to deep.

*Fruit stalk length*.—Medium to long, about 2.5 mm to 3 mm.

*Fruit stalk diameter*.—About 2 mm.

*Fruit stalk color*.—Close to 176A.

*Fruit skin color*.—Ground color is yellow, close to 10A to 10B; 90% of the area is overlain with red, close to 46A to 46B.

*Lenticels*.—Quantity: Medium, about 150 per fruit. Length: About 2 mm to 3 mm.

*Flesh texture*.—Firm, compact.

*Flesh color*.—Close to 10D.

*Flavor*.—Rich, aromatic.

*Locules*.—Quantity per fruit: Five. Length: About 2 cm. Width: About 1 cm. Shape: Ovate.

*Seeds*.—Quantity per locule: None to about three depending on environmental conditions. Length: About 5 mm to 7 mm. Diameter: About 3 mm to 5 mm. Color: Close to 200A.

Temperature tolerance: The new Apple tree has been observed to tolerate temperatures ranging from about −20 C to about 35 C.

Pathogen & pest resistance: To date, trees of the new Apple have not been observed to be resistant to pathogens and pests common to Apple trees.

It is claimed:

1. A new and distinct Apple tree named 'GALA MGCP' as illustrated and described.

* * * * *